(12) United States Patent
Fukuzumi (10) Patent No.: US 8,436,242 B2
(45) Date of Patent: May 7, 2013

(54) PHOTOCHARGE SEPARATION USING SUPRAMOLECULAR COMPLEX OF π-ELECTRON TYPE EXTENDED VIOLOGEN DERIVATIVE AND PORPHYRIN

(75) Inventor: Shunichi Fukuzumi, Mino-shi (JP)

(73) Assignee: Japan Science and Technology Agency (JP)

( * ) Notice: Subject to any disclaimer, the term of this patent is extended or adjusted under 35 U.S.C. 154(b) by 1185 days.

(21) Appl. No.: 10/592,037

(22) PCT Filed: Mar. 9, 2005

(86) PCT No.: PCT/JP2005/004134
§ 371 (c)(1),
(2), (4) Date: May 23, 2007

(87) PCT Pub. No.: WO2005/087741
PCT Pub. Date: Sep. 22, 2005

(65) Prior Publication Data
US 2008/0202578 A1    Aug. 28, 2008

(30) Foreign Application Priority Data
Mar. 10, 2004    (JP) ................. 2004-068247

(51) Int. Cl.
C07D 487/22    (2006.01)
B01J 31/00    (2006.01)
C01B 3/02    (2006.01)
H01L 31/00    (2006.01)

(52) U.S. Cl.
USPC ........... 136/252; 136/263; 540/145; 502/173; 204/157.52

(58) Field of Classification Search ................ 136/252, 136/263; 540/145; 502/173; 204/157.52
See application file for complete search history.

(56) References Cited

U.S. PATENT DOCUMENTS
2002/0040728 A1*    4/2002    Yoshikawa ................ 136/263

FOREIGN PATENT DOCUMENTS
| JP | 2000261016 A | 9/2000 |
|---|---|---|
| JP | 2001097977 A | 4/2001 |
| JP | 2002025635 A | 1/2002 |
| JP | 2003036896 A | 2/2003 |
| JP | 2005060304 A | 3/2005 |
| JP | 2005111297 A | 4/2005 |

OTHER PUBLICATIONS

Okura et al., "Photoredox properties of Viologen Linked Porphyrins", Bulletin of the Chemical Society of Japan, 1987.*

(Continued)

Primary Examiner — Jennifer Michener
Assistant Examiner — Matthew Martin
(74) Attorney, Agent, or Firm — Mintz Levin Cohn Ferris Glovsky and Popeo, P.C.; Ingrid A. Beattie (57) ABSTRACT

Long-lived charge separation is attained with high efficiency by using a supramolecular complex utilizing pi-pi interaction. A supramolecular complex is formed by pi-pi interaction between extended viologen, the extended viologen having heteroaryls coupled together by a linking group with pi-electron conjugated system, and porphyrin. As a result of study of photoelectron transfer reaction, it has been found that within the supramolecular complex, efficient electron transfer occurs from the singlet excited state of porphyrin to the extended viologen, thereby obtaining a charge separation condition of extremely long lifetime exceeding 1 millisecond.

4 Claims, 2 Drawing Sheets

OTHER PUBLICATIONS

Nanasawa et al., "Synthesis of viologens with extended pi-conjugation and their photochromic behavior on near IR absorption", Journal of Organic Chemistry, 2000.*

Dupuis et al., "Photoinduced intramolecular charge-transfer systems based on porphyrin dyads for optical limiting", Chemical Physics Letters, 1999.*

Ghosh et al., "Charge seperation, charge recombination and electron transfer reactions in solutions of fullerene-C60 and phenothiazines", Chemical Physics Letters, 1997.*

Wang et al., "Generating hydrogen by tin-porphyrin in microheterogeneous systems", Topics in Current Chemistry, 2002.*

Shelnutt, "Metal Effects on Metalloporphyring and on their pi-pi Charge Transfer complexes with aromatic acceptors", Inorganic Chemistry, 1983.*

Shelnutt. "Electronic Structure of the Porphyrin Ring in an Electrostatically Bound $\pi$-$\pi$ Complex." *J. Phys. Chem.* 88.25(1984):6121-6127.

Slama-Schwok. "Caroviologen Molecular Wires: Pulse Radiolysis of Bis(pyridinium) Polyenes." *J. Phys. Chem.* 96.25(1992):10559-10565.

* cited by examiner

PHOTOCHARGE SEPARATION USING SUPRAMOLECULAR COMPLEX OF π-ELECTRON TYPE EXTENDED VIOLOGEN DERIVATIVE AND PORPHYRIN

RELATED APPLICATIONS

This application is a national stage application, filed under 35 U.S.C. §371, of International Application No. PCT/JP2005/004134, filed on Mar. 9, 2005, which claims the benefit of and priority to Japan patent application 2004-068247 filed Mar. 10, 2004, the disclosure of each is incorporated by reference herein.

TECHNICAL FIELD

The present invention relates to a supramolecular complex of π-electron-system extended viologen and porphyrin. Also, the present invention relates to a photocharge separation method using the supramolecular complex. The supramolecular complex of the present invention is useful as an artificial photosynthetic reaction center molecule.

BACKGROUND ART

Conventionally, known artificial photosynthetic reaction center molecules are those in which an electron donor molecule and an electron acceptor molecule are linked by a covalent bond. For example, J. Phys. Chem. A 2002, 106, 3243-3252 (non-patent document 1) discloses a compound in which porphyrin and fullerene are linked by a covalent bond.

However, since it is cumbersome to synthesize a compound in which an electron donor molecule (donor) and an electron acceptor molecule (acceptor) are linked by a covalent bond, it is difficult to extend the compound to a more complex system.

On the other hand, numerous attempts have been made to form a supramolecular complex between an electron donor molecule and an electron acceptor molecule by using a non-covalent bond, so as to allow the supramolecular complex to function as an artificial photosynthetic reaction center. As compared with the use of covalent bond, the formation of a supramolecular using a non-covalent bond such as metal-ligand coordination or hydrogen bond is attracting more and more people's attention in recent years as a simple but elegant method of constructing a biological photosynthetic reaction center model system.

However, with these materials, there is the disadvantage that the charge-separated state cannot be maintained for a long period of time, so there has been a demand for a material that can be used as an artificial photosynthetic reaction center that can maintain the charge-separated state for a long period of time.

On the other hand, regarding weak π-π interaction, it has been considered that sufficient performance for a donor-acceptor-linked molecule cannot be obtained due to the weakness of its interaction. Therefore, supramolecular complexes using weak π-π interaction have not been studied.

Non-patent document 1: J. Phys. Chem. A 2002, 106, 3243-3252

DISCLOSURE OF THE INVENTION

Problems to be Solved by the Invention

An object of the present invention is to achieve a highly efficient and long-lived charge separation by using a supramolecular complex utilizing the weak π-π interaction.

Means for Solving the Problems

As a result of eager studies, the present inventors have found that a supramolecular complex is formed in benzonitrile by weak π-π interaction between the π-electron-system extended viologen serving as an acceptor and porphyrin serving as a donor. Also, the result of the studies on the photo-electron transfer reaction thereof unexpectedly shows that photoinduced electron transfer occurs efficiently from the singlet excited state of porphyrin to the extended viologen in this supramolecular complex, and a charge separated state having an extremely long lifetime exceeding 1 millisecond has been obtained.

Specifically, the present invention provides the following supramolecular complex, method of synthesizing a supramolecular complex, devices for converting light into electric energy, and others.

(1) A supramolecular complex formed with extended viologen and porphyrin, wherein the extended viologen is represented by the following general formula 1:

$$[R^1\text{-Het}^1\text{-(CH=CH)}_n\text{-Het}^2\text{-R}^2]^{2+} \quad \text{(Chemical formula 1)}$$

where, in the formula, $R^1$ and $R^2$ are independently hydrogen or an alkyl having a carbon number of 1 to 20; $Het^1$ and $Het^2$ are independently a heteroaryl; each heteroaryl contains a nitrogen atom as a heteroatom in the ring thereof; the nitrogen atom of $Het^1$ is bound to $R^1$; the nitrogen atom of $Het^2$ is bound to $R^2$; and n is 2 or 3.

(2) The supramolecular complex according to item 1, wherein said extended viologen is selected from any of the following formulas V-1 to V-6:

-continued

V-6

(3) The supramolecular complex according to item 2, wherein said extended viologen is expressed by the formula V-2.
(4) The supramolecular complex according to item 1, wherein said porphyrin has a phenyl group or a substituted phenyl group at 5-position, 10-position, 15-position, and 20-position thereof.
(5) The supramolecular complex according to item 1, wherein said porphyrin is selected from the following P-1 to P-4:

$Ar^3$: 3,5-di-t-butylphenyl

P-1

P-2: $Ar^1 = Ar^2 =$ 3,5-di-t-butylphenyl
P-3: $Ar^1 =$ H, $Ar^2 =$ 3,5-di-t-butylphenyl
P-4: $Ar^1 = Ar^2 =$ phenyl (6) The supramolecular complex according to item 5, wherein said extended viologen is the following V-2:

V-2

(7) The supramolecular complex according to item 6, wherein said $R^1$ and $R^2$ are $C_6H_{13}$.
(8) A method of synthesizing a supramolecular complex according to item 1, comprising a step of mixing said extended viologen and said porphyrin in a solvent.
(9) The method according to item 8, wherein said solvent is benzonitrile.
(10) A material for an artificial photosynthetic reaction center made of the supramolecular complex according to item 1.
(11) A hydrogen-producing photocatalyst containing the supramolecular complex according to item 1 and a platinum catalyst.
(12) A method of synthesizing hydrogen, comprising a step of irradiating water with light in the presence of a molecule serving as an electron source and a hydrogen-producing photocatalyst containing the supramolecular complex according to item 1 and a platinum catalyst.
(13) A device for converting light into electric current, wherein the device comprises the supramolecular complex according to item 1, and wherein the supramolecular complex is laminated on an electroconductive substrate.

Effects of the Invention

The present invention provides a supramolecular complex formed by weak π-π interaction. This supramolecular complex can generate a charge-separated state having an extremely long lifetime by photoexcitation. For this reason, the supramolecular complex of the present invention can be easily applied to a light energy conversion system. The present invention is the pioneer in achieving the function of an artificial photosynthetic reaction center by using a supramolecular complex utilizing the weak π-π interaction, which can be easily extended to a further complex system, thereby being far more excellent as compared with the conventional complexes using a covalent bond.

Since extended viologen can produce hydrogen from water in terms of energy when being subjected to one-electron reduction, it can be applied as a hydrogen-producing photocatalyst by combining the supramolecular complex of the present invention with a platinum catalyst.

BEST MODE FOR CARRYING OUT THE INVENTION (Porphyrin)
The porphyrin used in the present invention may be a non-substituted porphyrin or may be one having arbitrary substituents within a scope that does not deteriorate its performance as a porphyrin. For example, the porphyrin may have, as a substituent, an alkyl, an aryl, an alkyl-substituted aryl, or a halogen-substituted aryl at 5-position, 10-position, 15-position, and 20-position in the porphyrin, in other words, at the carbon atom of the methine group between a pyrrole ring and a pyrrole ring. This substituent is preferably a phenyl or a substituted phenyl, more preferably a phenyl, an alkyl- substituted phenyl, or a halogen-substituted phenyl, still more preferably a phenyl, a dialkyl-substituted phenyl, or a dichloro-substituted phenyl, particularly preferably a phenyl, a 3,5-di-tert-butylphenyl, or 2,6-dichlorophenyl. It is noted that the 5-position, the 10-position, the 15-position, and the 20-position of the porphyrin preferably all have the same substituent; however, two to four kinds of substituents may be introduced to the four positions of 5-position, 10-position, 15-position, and 20-position if necessary.

A preferred example of porphyrin is shown below.

Ar³: 3,5-di-t-butylphenyl

P-1

P-2: Ar¹ = Ar² = 3,5-di-t-butylphenyl
P-3: Ar¹ = H, Ar² = 3,5-di-t-butylphenyl
P-4: Ar¹ = Ar² = phenyl The porphyrin used in the present invention is preferably one having two hydrogen atoms at the central moiety surrounded by the four pyrrole rings thereof, as in the aforementioned P-1 to P-4 and the like. However, it may have a metal atom (for example, zinc atom) at the central moiety.

(Extended Viologen)

The extended viologen used in the present invention is a compound in which an alkyl-substituted heteroaryl and an alkyl-substituted heteroaryl are linked by a linking group that can form a conjugated system of π-electrons, whereby the two heteroaryl rings and the linking group together form one π-electron conjugated system, and is shown by the following general formula.

$$[R^1\text{-Het}^1\text{-}(CH=CH)_n\text{-Het}^2\text{-}R^2]^{2+} \qquad \text{(Chemical formula 1)}$$

In the formula, $R^1$ and $R^2$ are independently hydrogen or an alkyl having a carbon number of 1 to 20, preferably an alkyl having a carbon number of 2 to 15, more preferably an alkyl having a carbon number of 4 to 12, still more preferably an alkyl having a carbon number of 6 to 10. In one preferred embodiment, $R^1$ and $R^2$ are an alkyl having a carbon number of 6. Further, the alkyl may be a straight chain or a branched chain. Please note that $R^1$ and $R^2$ may be the same or may be different. It is preferable that $R^1$ and $R^2$ are the same in view of facility in synthesis.

$Het^1$ and $Het^2$ are independently a heteroaryl, and each heteroaryl contains a nitrogen atom as a heteroatom in the ring thereof. $Het^1$ and $Het^2$ are preferably pyridyl or a condensed ring obtained by condensation of pyridyl with a phenyl ring (for example, quinolyl, isoquinolyl, benz[h]isoquinolyl, or the like). Preferably $Het^1$ and $Het^2$ are pyridyl or quinolyl, more preferably pyridyl.

Here, with regard to positional relationship with the linking group, the pyridyl may be any of 2-pyridyl, 3-pyridyl, and 4-pyridyl. In one preferable embodiment, the pyridyl is 4-pyridyl.

Further, the aforesaid quinolyl may be any one of 2-quinolyl, 3-quinolyl, 4-quinolyl, 5-quinolyl, 6-quinolyl, 7-quinolyl, and 8-quinolyl. Preferably, the quinolyl is 2-quinolyl, 3-quinolyl, or 4-quinolyl. More preferably, the quinolyl is 2-quinolyl or 4-quinolyl.

Further, the aforesaid isoquinolyl may be any one of 1-isoquinolyl, 3-isoquinolyl, 4-isoquinolyl, 5-isoquinolyl, 6-isoquinolyl, 7-isoquinolyl, and 8-isoquinolyl. Preferably, the isoquinolyl is 1-isoquinolyl, 3-isoquinolyl, or 4-isoquinolyl.

$Het^1$ and $Het^2$ may be the same or different. When $Het^1$ and $Het^2$ are the same, the synthesis is facilitated.

The nitrogen atom of $Het^1$ is bound to $R^1$. The nitrogen atom of $Het^2$ is bound to $R^2$. The number n is 2 or 3. In one preferable embodiment, n is 2.

Extended viologen can be synthesized by an arbitrary known method. For example, P. Carsky et al., Liebigs Ann. Chem. 1980, 291-304 describes a method of synthesizing Het-$(CH=CH)_2$-Het by using Het-$CH_2$—$P^+Ph_3$ as a raw material and a method of synthesizing Het-$(CH=CH)_3$-Het by using Het-CHO and $(EtO)_2P(=O)CH_2$—CH=CH—$CH_2$—$P(=O)(OEt)_2$ as a raw material, and other methods.

Please note that in the present specification, extended viologen may be described as a viologen derivative; however, extended viologen is not limited to compounds derived from viologen, so that, as disclosed in the above document, extended viologen can be synthesized by using an arbitrary heteroaryl compound as raw material.

(Solvent)

The solvent used in the method of the present invention is not particularly limited as long as the solvent can dissolve the porphyrin serving as raw material and the extended viologen. The solvent is preferably benzonitrile.

(Formation of a Supramolecular Complex of Porphyrin and Extended Viologen)

By mixing the porphyrin and the extended viologen in a suitable solvent, a supramolecular complex can be formed.

The concentration of extended viologen at the time of mixing is not particularly limited; however, the concentration is preferably $1\times10^{-5}$ M or higher, more preferably $1\times10^{-4}$ M or higher, especially preferably $1\times10^{-3}$ M or higher. Further, the concentration is preferably $1\times10^{-1}$ M or lower, more preferably $5\times10^{-2}$ M or lower, especially preferably $1\times10^{-2}$ M or lower. When the concentration is too low, the yield of the supramolecular complex will be small. When the concentration is too high, it will likely be difficult to dissolve the extended viologen.

The concentration of the porphyrin at the time of mixing is not particularly limited; however, the concentration is preferably $1\times10^{-9}$ M or higher, more preferably $1\times10^{-8}$ M or higher, especially preferably $1\times10^{-7}$ M or higher. Further, the concentration is preferably $1\times10^{-4}$ M or lower, more preferably $1\times10^{-5}$ M or lower, especially preferably $1\times10^{-6}$ M or lower. When the concentration is too low, the yield of the supramolecular complex will be small. When the concentration is too high, it will likely be difficult to dissolve the porphyrin.

The molar ratio of mixing the porphyrin and the extended viologen is not particularly limited. They can be mixed at an arbitrary molar ratio. It is preferable that extended viologen is largely excessive relative to the porphyrin. With respect to 1 mol of the porphyrin, the extended viologen is preferably $1\times10$ mol to $1\times10^5$ mol, more preferably $1\times10^2$ mol to $1\times10^4$ mol, still more preferably $1\times10^3$ mol to $5\times10^3$ mol.

(Photoinduced Electron Transfer Reaction of Supramolecular Complex)

It is possible to use the supramolecular complex of the present invention for performing a photoinduced electron transfer reaction. The photoinduced electron transfer reaction of a supramolecular complex can be confirmed by the method described in the later-described Examples or the like.

(Light Energy Conversion Material)

In the present specification, a light energy conversion material refers to a material that converts light into electric energy. The light energy conversion material is usable in devices such as a solar cell and a photosensor. An device having an excellent performance can be produced by using the material of the present invention in a known production method with respect to these devices.

(Material for an Artificial Photosynthetic Reaction Center)

The supramolecular complex of the present invention can be used as a material for an artificial photosynthetic reaction center. Conventionally, a known material for an artificial photosynthetic reaction center is obtained by covalently bonding an electron donor molecule and an electron acceptor molecule. Similarly to a conventional material used for an artificial photosynthetic reaction center, the supramolecular complex of the present invention can be used as an artificial photosynthetic reaction center.

(Hydrogen-Producing Photocatalyst)

The supramolecular complex of the present invention can be used for a hydrogen-producing photocatalyst. Conventionally, a known hydrogen-producing photocatalyst is obtained by combining a water-reducing catalyst and a porphyrin derivative. By using the supramolecular complex of the present invention in place of the porphyrin derivative of the conventional catalyst, a hydrogen-producing photocatalyst of the present invention can be obtained. For example, by laminating a platinum catalyst on a substrate such as glass and by further laminating a supramolecular complex thereon, a hydrogen-producing catalyst can be formed.

(Hydrogen Synthesis Method)

The supramolecular complex of the present invention can be used in a hydrogen synthesis method. For example, by irradiating water with light in the presence of a molecule serving as an electron source and a hydrogen-producing photocatalyst containing a supramolecular complex and a platinum catalyst, water can be reduced to generate hydrogen. The molecule serving as an electron source can be an arbitrary compound, such as molecule that can give electrons to an excited state of a photocatalyst. Specifically, an analog of dihydronicotinamide adenine dinucleotide (NADH), which is an important electron source in the living body such as 1-benzyl-1,4-dihydronicotinamide and the like can be used.

(Device)

The supramolecular complex of the present invention can be effectively used as a material for a conventionally known device that converts lights into electric current. For example, it can be used as a material for a photoelectric conversion device. The construction of the device can adopt an arbitrary construction conventionally known in the art. For example, by laminating a supramolecular complex on an electroconductive substrate, a device that converts light into electric current can be obtained.

EXAMPLES

Hereafter, non-limiting Examples of the present invention will be described.

(Preparation of Supramolecular Complex)

A π-electron-system extended viologen, $BHV^{2+}$, which has a π-system extended with a butadiene skeleton, was used. Further, for comparison, viologen having no butadiene skeleton ($HV^{2+}$) was used.

The porphyrins used were the aforementioned four types of porphyrins P-1 to P-4.

The porphyrins from P-1 to P-4 were synthesized in accordance with the method described in the literature, and were characterized by the $^{13}C$ NMR spectrum and MALDI-TOF MS spectrum. Further, the extended viologen ($BHV^{2+}$) was synthesized in accordance with the method described in the literature (P. Carsky et al., Liebigs Ann. Chem. 1980, 291-304). Further, the viologen ($HV^{2+}$) was synthesized in accordance with a method described in the literature.

Figure 1:
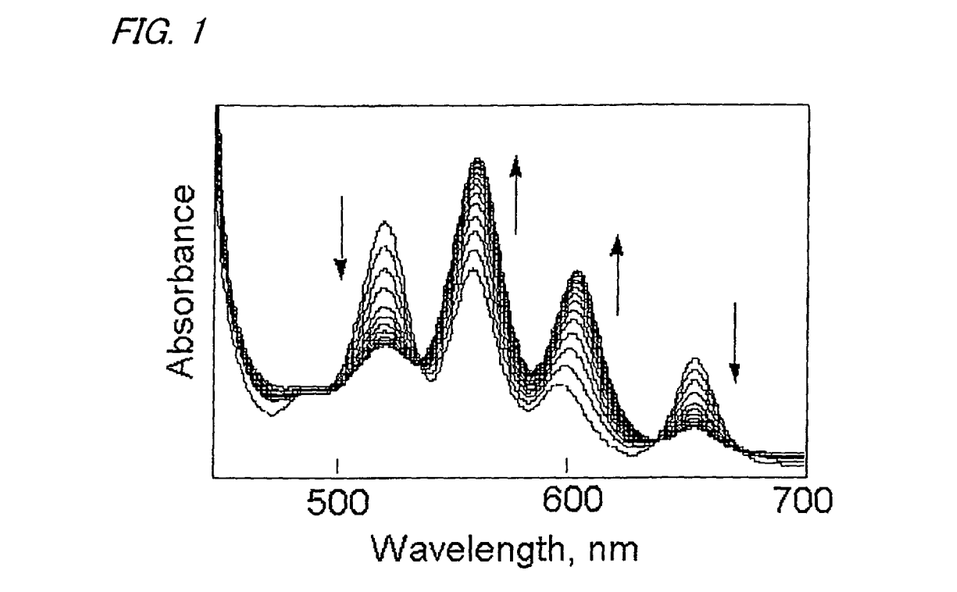
FIG. 1 shows a UV-visible absorption spectra of P-1 ($6 \times 10^{-7}$ M) in the presence of various concentrations of $BHV^{2+}$ (0 to $5 \times 10^{-3}$ M) in PhCN.

Various concentrations of $BHV^{2+}$ were added to a benzonitrile (PhCN) solution of porphyrin (P-1), and ultraviolet-visible absorption spectral changes of porphyrin were studied. The spectrum changed while having isosbestic points. FIG. 1 shows a UV-vis absorption spectrum of porphyrin P-1 ($6\times10^{-7}$ M) mixed with various concentrations of $BHV^{2+}$ (0 to $5\times10^{-3}$ M) in PhCN.

By photoexcitation of the Soret band of porphyrin at 430 nm in PhCN, fluorescences at $\lambda_{max}$=612 nm and 652 nm were generated. Addition of $BHV^{2+}$ to a PhCN solution of porphyrin generated a significant decrease in the fluorescence intensity. Such a decrease in the fluorescence intensity change is due to photoinduced electron transfer from the singlet excited state of porphyrin to $BHV^{2+}$ in the supramolecular porphyrin complex formed between the porphyrin and $BHV^{2+}$.

A similar experiment was conducted using $HV^{2+}$ in place of $BHV^{2+}$. However, in that case, spectrum change such as in the case of using $BHV^{2+}$, was not observed. That is, the complex due to π-π interaction was formed only when $BHV^{2+}$ was used.

(Photoinduced Electron Transfer Reaction)

Figure 2:
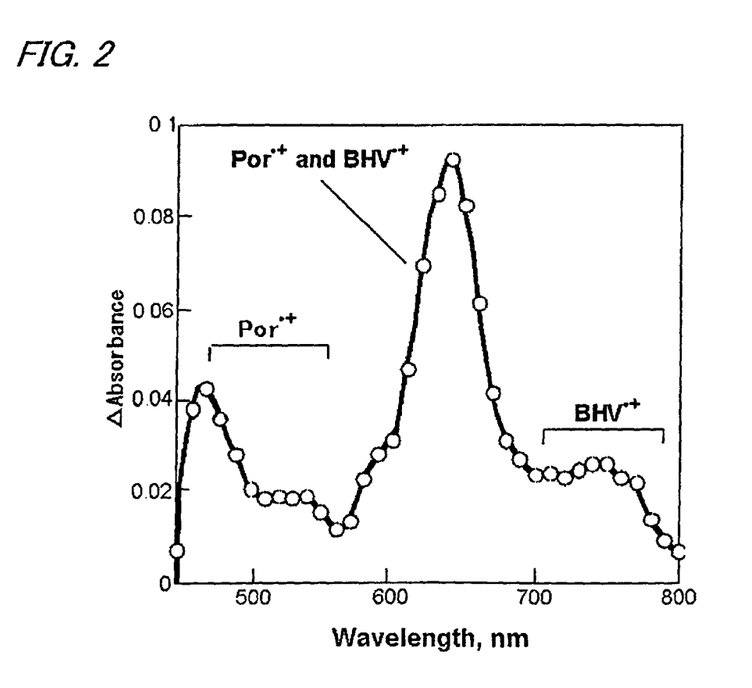
FIG. 2 shows a transient absorption spectrum of P-1 ($2.0 \times 10^{-6}$ M) in deaerated PhCN at 298K in the presence of $BHV^{2+}$ ($5.0 \times 10^{-3}$ M), as measured at 20 μs after the laser excitation at 430 nm.

The generation of photoinduced electron transfer in the supramolecular complex $BHV^{2+}$-$(P-1)^+$ was been confirmed by transient absorption spectrum of porphyrin-$BHV^{2+}$ π-complex in PhCN using nanosecond laser flash photolysis, as shown in FIG. 2. The transient absorption bands observed in FIG. 2 agree with superposition of absorption bands due to porphyrin radical cation and the absorption band of $BHV^{2+}$ in PhCN. Therefore, the transient absorption spectrum of FIG. 2 clearly shows formation of the CS state of porphyrin-BHV$^{2+}$ π-complex by photoinduced electron transfer from the singlet excited state of porphyrin to BHV$^{2+}$ in the supramolecular complex.

FIG. 2 shows a transient absorption spectrum of P-1 (2.0× 10$^{-6}$ M) at 298K in the presence of BHV$^{2+}$ (5.0×10$^{-3}$ M), as measured at 20 μs after the laser excitation at 430 nm in deaerated PhCN.

Figure 3:
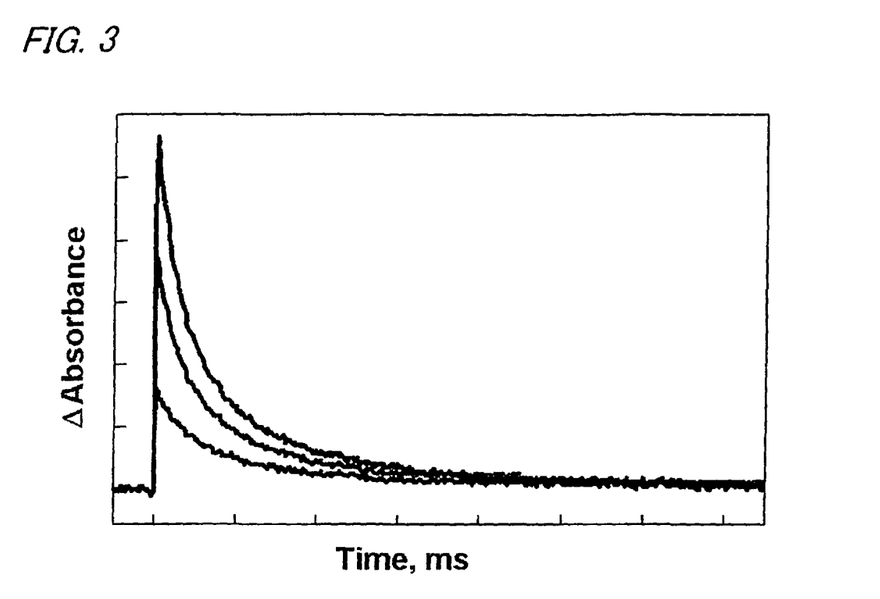
FIG. 3 shows a time profile of absorption at 640 nm due to the CS state obtained upon nanosecond flash photolysis with different laser power (10 mJ, 2.2 mJ, and 0.5 mJ) at 298K in deaerated PhCN.

The decay of absorption due to the CS state detected in FIG. 2 obeyed the first-order kinetics based on intramolecular back electron transfer returning to the ground state FIG. 3 shows a time profile of absorption at 640 nm due to the CS state obtained upon nanosecond flash photolysis with different laser power (10 mJ, 2.2 mJ, and 0.5 mJ) at 298K in deaerated PhCN.

Figure 4:
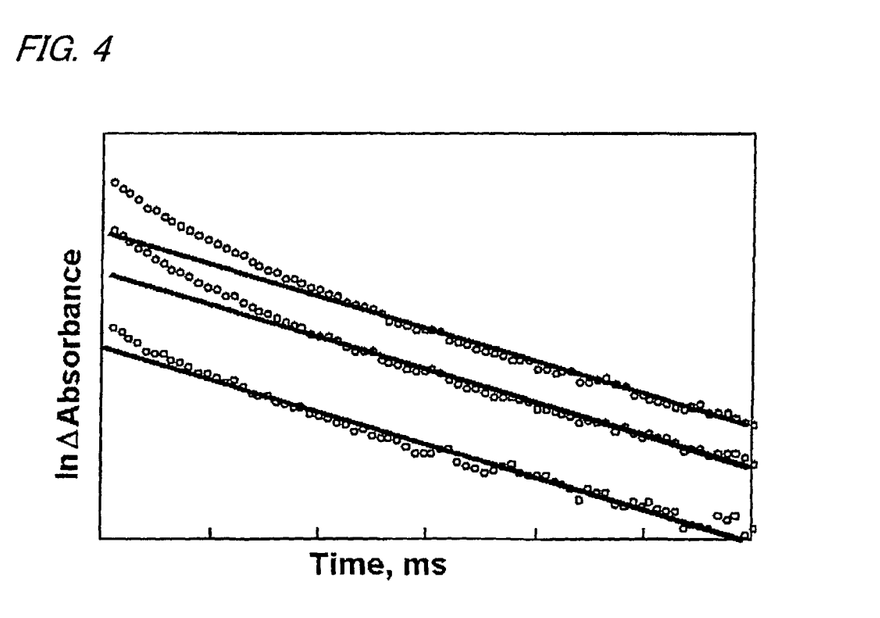
FIG. 4 shows first-order plots of decay of absorbance at 620 nm (10 mJ, 2.2 mJ, and 0.5 mJ).

FIG. 4 shows first-order plots of decay of absorption at 620 nm (10 mJ, 2.2 mJ, and 0.5 mJ). The first-order plots of various initial CS concentrations afforded linear correlation having the same slope.

Thus, this decay process is ascribed to back electron transfer in the supramolecular complex rather than the intermolecular back electron transfer between the porphyrin radical cation and BHV$^+$ generated by the intermolecular photoinduced electron transfer.

The lifetime of the CS state of the porphyrin (P-1)-BHV$^{2+}$ π-complex was determined to be 1.4 ms at 298K in PhCN. This is the longest of the lifetimes of the CS state reported, with regard to the donor-acceptor dyad that has been bound by covalent bond or non-covalent bond in a solution. Therefore, this system is widely applicable for development of an efficient solar light energy conversion system.

With regard to the porphyrins P-2 to P-4, experiments were conducted in the same manner as in the above-described porphyrin P-1. The results confirmed the formation of a supramolecular complex in the same manner as in P-1, thereby confirming the CS state having a long lifetime.

INDUSTRIAL APPLICABILITY

The present invention is the first example in which a supramolecular complex formed by π-π interaction generates a charge-separated state having an extremely long lifetime by photoexcitation, and is important as a system that facilitates application to a light energy conversion system.

Viologen can produce hydrogen from water in terms of energy when subjected to one-electron reduction, and therefore it is applicable as a hydrogen-producing photocatalyst when combined with a platinum catalyst.

As described above, the present invention has been illustrated using the preferred embodiments of the present invention. However, the present invention should not be construed to be limited to these embodiments. It is understood that the scope of the present invention should be construed solely on the basis of the claims. It is understood that those skilled in the art can carry out an invention within the scope equivalent to the description of the specification, based on the description of the specific preferred embodiments, the description of the present invention and the common technical knowledge. It is understood that the patents, patent applications, and other documents cited in the present specification should be incorporated by reference in the present specification as if the contents thereof are specifically described herein.

The invention claimed is:

1. A supramolecular complex comprising extended viologen and porphyrin, wherein the extended viologen is selected from any of the following formulas V-1 to V-6:

V-1

V-2

V-3

V-4

V-5

V-6 wherein, R$^1$ and R$^2$ are independently hydrogen or an alkyl having from 1 to 20 carbons; and n is 2 or 3, and wherein said porphyrin is P-1:

Ar$^3$: 3,5-di-t-butylphenyl

P-1

-continued

P-2: $Ar^1 = Ar^2$ = 3,5-di-t-butylphenyl
P-3: $Ar^1$ = H, $Ar^2$ = 3,5-di-t-butylphenyl
P-4: $Ar^1 = Ar^2$ = phenyl wherein the supramolecular complex is formed by π-π interaction between the extended viologen and the porphyrin.

2. The supramolecular complex according to claim 1, wherein the extended viologen is V-2.

3. The supramolecular complex according to claim 2, wherein said $R^1$ and $R^2$ are $C_6H_{13}$.

4. The supramolecular complex according to claim 3, wherein n is 2.

* * * * *

UNITED STATES PATENT AND TRADEMARK OFFICE
CERTIFICATE OF CORRECTION

PATENT NO. : 8,436,242 B2
APPLICATION NO. : 10/592037
DATED : May 7, 2013
INVENTOR(S) : Shunichi Fukuzumi It is certified that error appears in the above-identified patent and that said Letters Patent is hereby corrected as shown below:

In the Claims:

Claim 1, at column 10, line 47, the text reading "2or 3" should read --2 or 3--.

Claim 1, at column 11, lines 1-18, the structure and text should be deleted:

" ".

Signed and Sealed this
Eighteenth Day of June, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,436,242 B2 | Page 1 of 1 |
| APPLICATION NO. | : 10/592037 | |
| DATED | : May 7, 2013 | |
| INVENTOR(S) | : Fukuzumi | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1232 days.

Signed and Sealed this
Thirtieth Day of December, 2014

Michelle K. Lee
*Deputy Director of the United States Patent and Trademark Office*